(12) United States Patent
Laguna

(10) Patent No.: US 6,773,447 B2
(45) Date of Patent: Aug. 10, 2004

(54) BALLOON CATHETER AND TREATMENT APPARATUS

(75) Inventor: Alvaro J. Laguna, Flagstaff, AZ (US)

(73) Assignee: Sentient Engineering & Technology, LLC, Flagstaff, AZ (US)

( * ) Notice: Subject to any disclaimer, the term of this patent is extended or adjusted under 35 U.S.C. 154(b) by 0 days.

(21) Appl. No.: 10/187,923

(22) Filed: Jul. 2, 2002

(65) Prior Publication Data
US 2004/0006359 A1 Jan. 8, 2004

(51) Int. Cl.$^7$ .............................................. A61M 29/00
(52) U.S. Cl. ..................................................... 606/198
(58) Field of Search ....................... 604/101.01, 101.02, 604/101.03; 606/192–198

(56) References Cited

U.S. PATENT DOCUMENTS

| | | | |
|---|---|---|---|
| 4,637,396 A | 1/1987 | Cook | |
| 4,706,670 A | 11/1987 | Andersen et al. | |
| 5,019,042 A | * 5/1991 | Sahota | 604/101.01 |
| 5,112,304 A | * 5/1992 | Barlow et al. | 606/194 |
| 5,619,903 A | 4/1997 | Rogers et al. | |
| 5,647,848 A | 7/1997 | Jorgensen | |
| 5,752,934 A | 5/1998 | Campbell et al. | |
| 5,833,657 A | * 11/1998 | Reinhardt et al. | 604/101.02 |
| 5,868,704 A | 2/1999 | Campbell et al. | |
| 6,120,477 A | 9/2000 | Campbell et al. | |
| 6,156,254 A | 12/2000 | Andrews et al. | |
| 6,183,505 B1 | 2/2001 | Mohn, Jr. et al. | |
| 6,632,235 B2 | * 10/2003 | Weikel et al. | 606/192 |

FOREIGN PATENT DOCUMENTS

EP 0331040 B1 12/1991

* cited by examiner

Primary Examiner—Kevin T. Truong
(74) Attorney, Agent, or Firm—Gary R. Jarosik; Mark R. Galis

(57) ABSTRACT

The present invention provides an improved balloon catheter. The balloon is of a composite material having the flexibility and elastic characteristics of an elastomeric material, yet exhibiting the growth limits of inelastic materials. The balloon may be treated to maintain a substantially constant length during inflation and deflation. The balloon may be provided with regions of porosity for the delivery of therapeutic agents, and may be treated to exhibit regions of distinct compliance. Also disclosed is an apparatus, which may be used to impart the regions of distinct compliance into the balloon.

83 Claims, 5 Drawing Sheets

BALLOON CATHETER AND TREATMENT APPARATUS

FIELD OF INVENTION

The present invention generally relates to balloon catheters.

BACKGROUND OF THE INVENTION

Various types of balloon catheters are routinely employed in medical procedures. Typically, balloon catheters consist of elongate thin-walled tubular catheter assemblies with an inflatable balloon attached at the distal end.

Balloon catheters are commonly used to dilate or remove constrictions, or to deliver and deploy other devices within bodily conduits. In the treatment of constricted conduits, the balloon catheter is inserted within the patient and navigated through the conduit (such as a blood vessel) to the site of blockage. The balloon at the distal end of the catheter is then inflated, causing the balloon to increase in diameter until the desired therapeutic result is achieved. Once the blockage is opened, the balloon is deflated and removed from the patient.

In a similar fashion, devices such as stents are typically secured onto the distal ends of balloon catheters, the catheters used to deliver the stent to the site of a blockage. Once at the desired location, the underlying balloon is inflated, causing the stent to increase in diameter and thus remodel and support the tissue, which constitutes the blockage within the bodily conduit. Once the therapeutic result is achieved the balloon is deflated and removed from the patient, leaving the stent implanted.

Balloon catheters may employ various balloon materials depending on the application for which they are used. For example, embolectomy balloon catheters utilize elastomeric balloon materials such as latex or silicone because in such procedures there is no need for the use of high inflation pressures. Angioplasty balloon catheters, on the other hand, utilize relatively inelastic materials such as polyester or nylon because in such procedures the application of high inflation pressure is often required.

Elastomeric and inelastic balloon materials each have advantages and drawbacks. While elastomeric materials are generally soft and conformable, they lack strength and exhibit continuous diameter growth with the application of increasing inflation pressure until rupture occurs. Elastomeric balloon materials are referred to as compliant. Inelastic balloon materials have very predictable diameter growth characteristics, and distend very little beyond their intended diameter with the application of increasing inflation pressure. Inelastic balloon materials are referred to as non-compliant or semi-compliant depending on their stiffness.

Due to their stiffness, inelastic balloon materials are not soft and conformable. Balloons made of these materials, such as angioplasty balloons, are carefully wrapped into a small cross-sectional configuration prior to introduction into the patient. During inflation, the balloons unwrap and assume their intended diameters. During subsequent deflation, however, the balloons do not return to their initial small cross-sectional state.

Angioplasty balloons are often difficult to maneuver through tortuous bodily conduits, posing a challenge in the treatment of blockages within small conduits such as within the coronary vasculature or the neurovasculature. Further, when inflated within a curved conduit, such balloons tend to straighten the conduit because of their lack of conformability. This straightening can result in localized trauma.

The delivery of devices such as stents via angioplasty balloon catheters can be problematic due to inadequate securement of the stent onto the balloon. The inelastic materials do not provide adequate engagement to the stent, leaving the stent prone to slipping along the length or completely off of the balloon. Also, because the inelastic materials are essentially non-compressible, the edges of a stent, when mounted onto a balloon made of such materials are exposed and vulnerable to being damaged during navigation through narrowed tortuous conduits.

In addition to the drawbacks mentioned above, there are complications associated with the mechanics of folded balloons. As described, angioplasty balloons are typically folded or wrapped about the catheters to which they are attached. During use, the balloons unfold at very low pressure. In the presence of an obstruction within a conduit, particularly if the obstruction is centered within the length of the balloon, such balloons tend to unfold very quickly at the ends where diameter growth is unimpeded, forming an hourglass shape. As the balloon is inflated to greater pressures, the obstructive tissue is remodeled toward the center of the balloon length, creating a densified lesion and a generally insufficient vessel inner diameter. Similar mechanics may occur during inflation of a stent, particularly if the length of the stent is not carefully matched to the length of the balloon.

In many cases, blockages occur close to the junction of two conduits. In such situations, particularly if the lesion is located at one end of the balloon, the mechanics described above, rather than densifying the obstructive tissue towards the center of the balloon, redistribute the occlusive tissue into the junction between the two conduits, thus compromising the junction and creating an obstruction within the branching conduit.

Another complication of balloon angioplasty and stenting is the formation of emboli. Embolic episodes occurring in various anatomical locations, particularly the brain can result in potentially debilitating outcomes or even death.

SUMMARY OF THE INVENTION

The present invention is an improved balloon catheter. The balloon catheter of the present invention comprises a composite balloon material attached to a catheter assembly. The balloon material has the flexibility and elastic characteristics of an elastomeric material, but also has a well-defined growth limit such as exhibited by inelastic balloon materials. The balloon material may be manufactured to maintain a substantially constant length during inflation and subsequent deflation. Various embodiments of the balloon material may be produced to be liquid tight or may be produced with one or more regions of porosity through which various therapeutic agents may be delivered. Additionally, the balloon material may be manufactured with regions of distinct inflation characteristics (compliance) such that one or more regions of the balloon inflate at a faster rate than the remaining region(s). Regions of distinct compliance provide enhanced control during angioplasty and stenting procedures and may be beneficial in reducing the creation of emboli during such procedures. The balloon catheter of the present invention may be provided with a balloon having a substantially constant diameter or may be provided with a balloon having a predetermined shape to further enhance angioplasty and stenting procedures.

Also disclosed is an apparatus, which may be used to instill the regions of distinct compliance within the balloon. The apparatus may be used to essentially customize the compliance of the balloon such that the balloon optimally serves the needs of the end user.

BRIEF DESCRIPTION OF EXEMPLARY DRAWINGS

Additional aspects of the present invention will be evident upon reviewing the non-limiting embodiments in the specification and the claims, in conjunction with the accompanying figures, where:

Figure 4A:
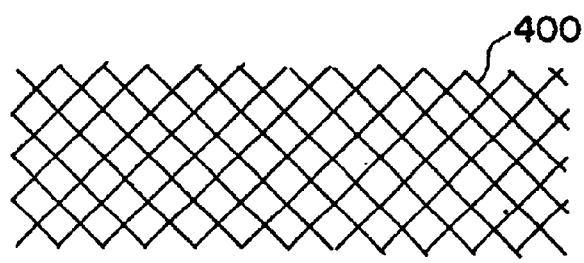
Figure 4B:
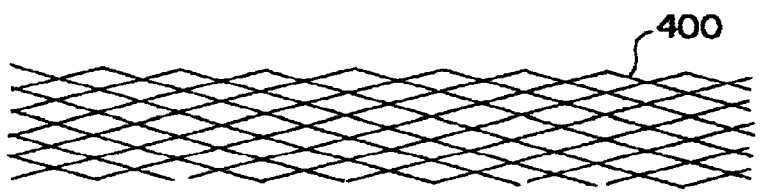
Figure 4C:
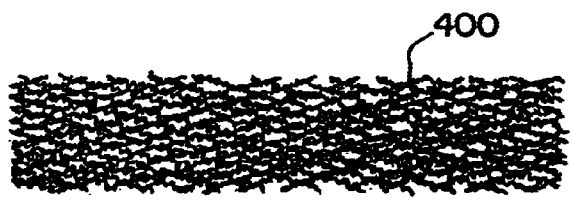
Figure 5:
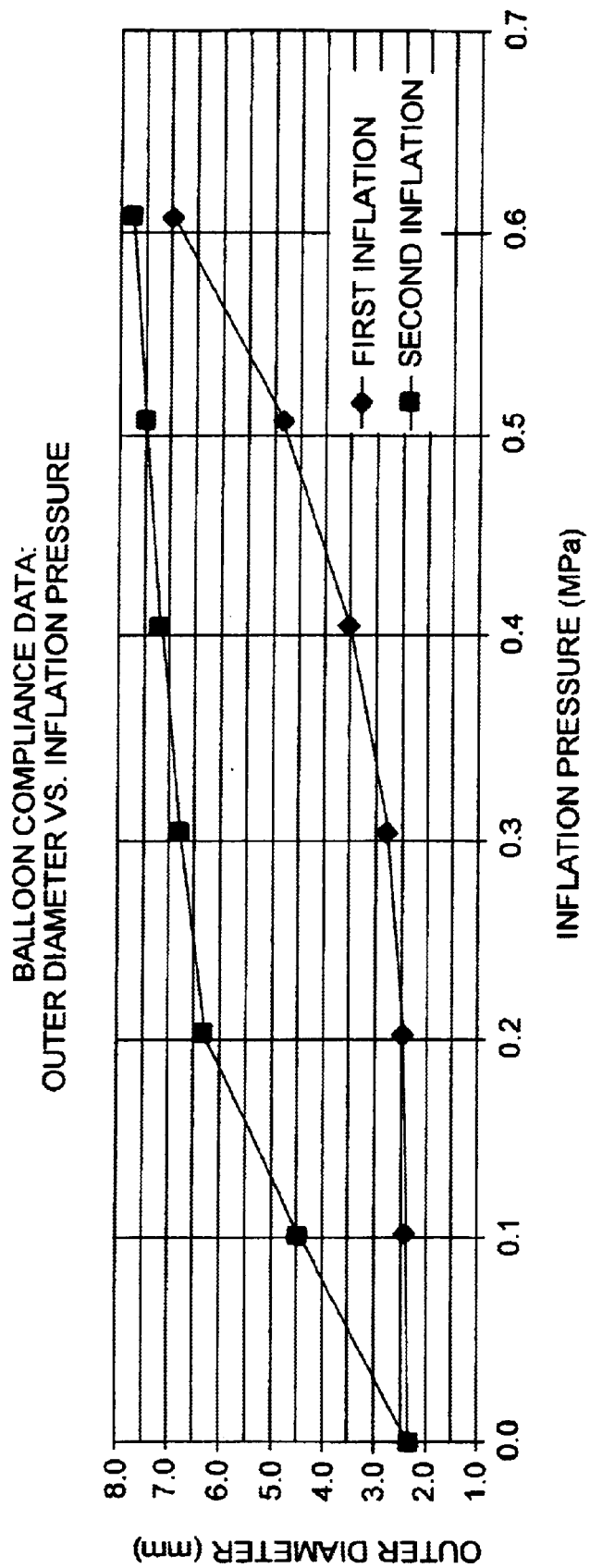
Figure 6A:
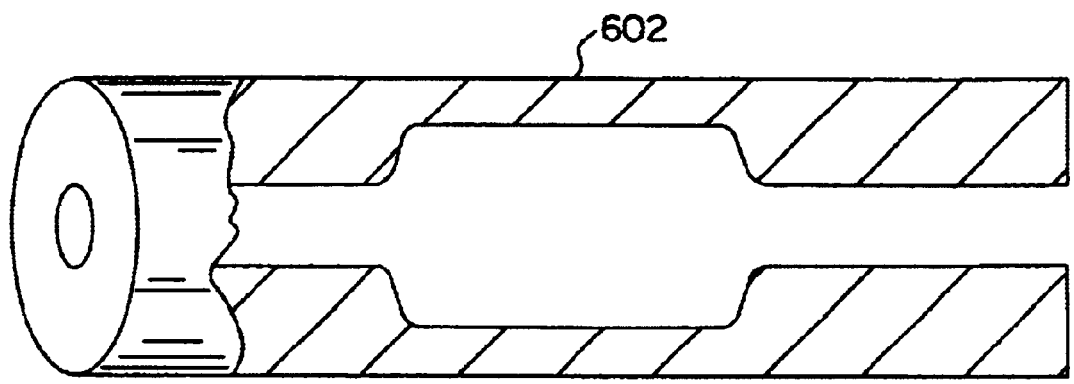
Figure 6B:
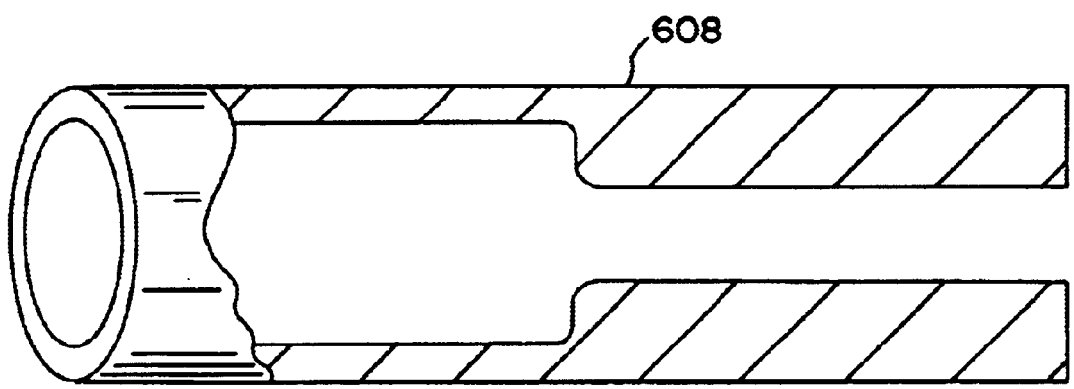

FIGS. 4A, 4B, and 4C are enlarged views of a braided tube used in the manufacture of an exemplary embodiment of the inventive balloon material;

FIG. 5 is a graph illustrating the compliance characteristics of an exemplary embodiment of the inventive balloon material; and FIGS. 6A and 6B are partial longitudinal cross-sectional views of exemplary embodiments of inflation molds that may be used to customize the compliance characteristics of the inventive balloon material.

DETAILED DESCRIPTION OF EXEMPLARY EMBODIMENTS

Figure 1:
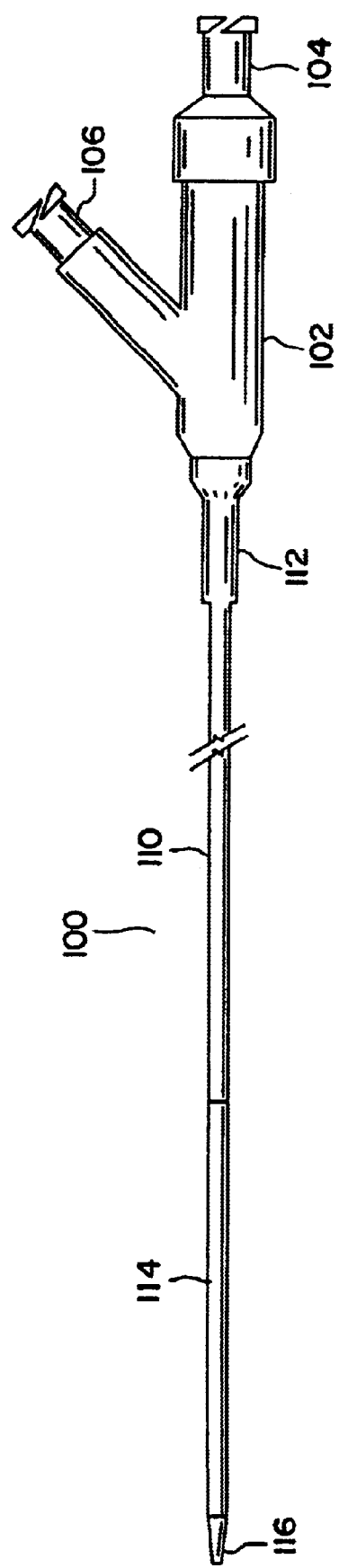
FIG. 1 is an elevational view of an exemplary balloon catheter of the present invention.

Referring to the figures, wherein like numerals designate like elements, illustrated in FIG. 1 is an exemplary embodiment of a balloon catheter 100 that includes a proximal adapter 102 located at the proximal end of the device. The proximal adapter includes a wire port 104 and a balloon port 106, both of which comprise a luer fitting for engagement with other accessory devices. The proximal adapter 102 is attached to an inner catheter member 108 (FIG. 2) and an outer catheter member 110. The two catheter members are arranged coaxially. The attachment between the proximal adapter 102 and the outer catheter member 110 is enhanced by strain relief member 112, which provides support to the outer catheter member 110, minimizing the tendency of the outer catheter member 110 to kink at or near the attachment point.

Figure 2:
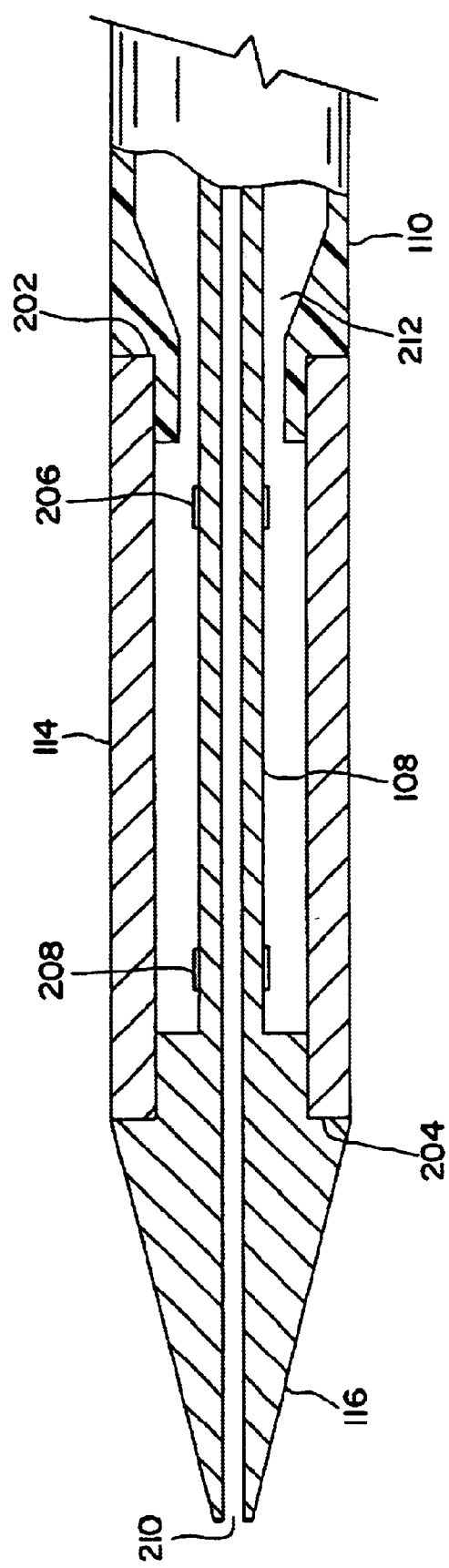
FIG. 2 is an enlarged partial longitudinal cross-sectional view of the distal portion of an exemplary balloon catheter of the present invention.

At the distal portion of the balloon catheter 100 is balloon 114. Balloon 114 is attached at its proximal end to outer catheter member 110 and at its distal end to inner catheter member 108 as illustrated in FIG. 2. Also, at the distal portion of balloon catheter 100 is distal tip 116, which comprises the distal end of inner catheter member 108.

Although the embodiment depicted by FIG. 1 comprises two catheter members arranged coaxially, any suitable catheter member arrangement may be employed. For example, a single, dual-lumen catheter member, having a lumen providing communication between the balloon port and the balloon, and another lumen capable of accommodating a guidewire may be employed. Additionally, the assembly of the catheter member(s) may be of any suitable configuration such as, but not limited to, fixed wire, wherein a wire element is included into the catheter tube(s) to add stiffness, over the wire (as depicted by FIG. 1), or rapid exchange.

The design and manufacture of catheter components and assemblies thereof is well known. Catheter members 108 and 110 may be of any suitable material or combination of materials such as, but not limited to, silicone, polyurethane, nylon, polyethylene, various coploymers such as PolyEther Block Amid (PEBA), or polytetrafluoroethylene (PTFE). In some embodiments catheter members 108 and 110 may suitably contain metallic elements such as, but not limited to, braids, hypodermic tubing and/or wires. Proximal adapter 102 may be configured in any suitable manner and may also be of any suitable material or combination of materials such as, but not limited to, nylon, polycarbonate, polypropylene, PEBA, or polysulfone. Any suitable method may be employed to create the attachments between the various elements of the balloon catheter 100. Such methods may include, but are not limited to, the use of various adhesives or thermal bonding techniques.

FIG. 2 illustrates an enlarged view of the arrangement of catheter members 108 and 110 as well as balloon 114 of the exemplary embodiment of balloon catheter 100. In this particular embodiment the distal end of outer catheter member 110 is provided with a step 202 which accommodates the proximal end of balloon 114 such that the outer surface of balloon 114 is flush with the outer surface of the outer catheter member 110. In a similar fashion, inner catheter member 108 is provided with step 204 which accommodates the distal end of balloon 114 such that the outer surface of balloon 114 is flush with the outer surface of distal tip 116 of the inner catheter member 108. Such an arrangement may be used to create a sleek profile to enhance navigation of the balloon catheter 100 through narrow, tortuous bodily conduits.

As shown by FIG. 2, inner catheter member 108 may be provided with radiopaque markers 206 and 208. These markers can be positioned so as to coincide with the edges of balloon 114 while the balloon is inflated, and to provide radiographic visualization of the balloon. Markers 206 and 208, in this embodiment, are configured as bands attached to inner catheter member 108. Any suitable configuration of markers 206 and 208 may be employed. Additionally, any suitable method of attaching the markers 206 to the inner catheter member 108 such as, but not limited to, the use of various adhesives, or swaging may be used. Also, markers 206 and 208 may be of any suitable material or combination of materials such as, but not limited to, gold, tantalum, or alloys of platinum and iridium. Markers 206 and 208 may also be printed onto inner catheter member 108 with radiopaque inks.

Inner catheter member 108 also includes a lumen 210, which may accommodate a guidewire to aid in navigation of the balloon catheter 100. In this exemplary embodiment, lumen 210 extends along the entire length of inner catheter member 108. Guidewire port 104 provides convenient access to lumen 210. Similarly, outer member 110 includes lumen 212, which provides communication between balloon port 106 and balloon 114 allowing balloon 114 to be inflated with, for example, saline.

Figure 3:
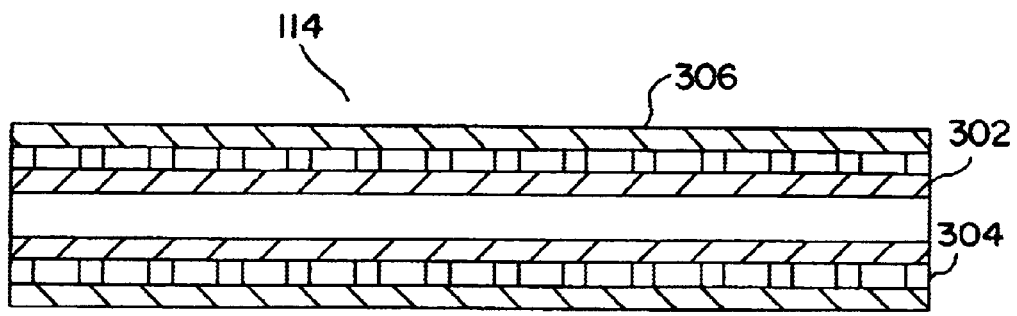
FIG. 3 is an enlarged longitudinal cross-sectional view of an exemplary embodiment of the inventive balloon material.

FIG. 3 depicts an enlarged cross-sectional view of an exemplary embodiment of the balloon 114 of the present invention. While the illustrated embodiment of balloon 114 comprises 3 layers, it is to be understood, however, that balloon 114 may comprise any suitable number of layers in any suitable manner. It is to be further understood that the layers need not be separate and distinct. Rather, the layers can be co-extruded. In the illustrated exemplary embodiment, inner layer 302 is comprised of silicone tubing having an inner diameter of approximately 1.2 mm and an outer diameter of approximately 1.4 mm.

To produce the exemplary balloon 114, an approximately 150 mm length of silicone tubing is fitted coaxially onto an approximately 1.19 mm diameter stainless steel rod. Isopropyl alcohol may be used as a lubricant to facilitate the fitting. With the silicone tubing fitted onto the rod, the rod is preferably placed within an air convection oven set at approximately 70° C. for approximately 10 minutes to evaporate any residual alcohol. While in this embodiment inner layer 302 is comprised of silicone tubing and is liquid tight, any suitable material or combination of materials such as, but not limited to, latex, polyurethane, PEBA, and/or fluoroelastomers may be used. Some embodiments of inner layer 302 may include regions of porosity that allow the passage of fluids there through while still allowing balloon 114 to be inflated. Additionally, various methods or combinations of methods may be employed to create a suitable inner layer 302. Such methods include, but are not limited to, dipping, application by spraying, and/or molding.

In this exemplary embodiment, the middle layer 304 comprises 2 layers of a treated braided tube 400. The 2 layers of treated braided tube 400 are intended to provide strength to the finished embodiment of balloon 114 such that the balloon achieves a well-defined inflation diameter beyond which minimal growth occurs. A suitable braided tube 400 is manufactured by Prodesco, Inc. of Perkasie, Pa. The tube is created from 144 individual strands of 9 denier monofilament polyester yarn, has a relaxed inner diameter of approximately 7 mm, a wall thickness of approximately 0.05 mm, and a braid density of 21.7 pixels per centimeter (55 pixels per inch).

FIG. 4A shows an enlarged illustration of the braid pattern of braided tube 400 in a relaxed state. Although this embodiment utilizes polyester braid material, any suitable material or combination of materials such as, but not limited to, nylon, polyethylene, carbon, kevlar, PEBA, and/or PTFE may be used. In some embodiments it may advantageous to combine thin metallic elements into the braid. Additionally, any suitable braid pattern with any suitable strand of any suitable denier, either monofilament, multifilament or any combination thereof may be used. The braid pattern may, for example, employ strands running parallel to the major axis of the tube. It should be understood that any suitable form of textile material or combination of forms such as, but not limited to, woven materials, non-woven materials, knitted materials and/or braided materials may be used to create a suitable middle layer 304. For example, some embodiments may utilize a textile other than a braid alone or in combination with a braid to create a suitable middle layer 304.

Middle layer 304 need not be in the form of a continuous tube and need not be a continuous layer throughout the entire length of the balloon 114. For example, narrow strips of suitable textiles may be arranged to create an embodiment of middle layer 304.

Alternatively, strips of textiles may be arranged helically to create an embodiment of middle layer 304. Some embodiments of balloon 114 may comprise a middle layer 304 in only a portion or portions of the balloon length. Also, some embodiments of balloon 114 may comprise a middle layer 304 that varies in thickness and/or strength along the length of the balloon.

As is typical for braided tubes, braided tube 400 exhibits a relationship between its diameter and its length. In order to treat the exemplary braided tube 400 such that it may increase in diameter with substantially no change in length, braided tube 400 is preferably fitted coaxially over an approximately 1.65 mm diameter stainless steel rod. Braided tube 400 is then axially elongated such that it reduces in diameter and fits snugly onto the outer surface of the rod. Each end of braided tube 400 is then secured to the rod with wire, maintaining the axially elongated/reduced diameter condition. FIG. 4B shows an enlarged illustration of the braid pattern of braided tube 400 in the axially elongated/reduced diameter condition.

With braided tube 400 secured to the rod, thin PTFE film is helically wrapped about the outer surface of the tube to further secure the tube to the stainless steel rod. The wrapping of the PTFE film may be completed manually, with minimal tension. The wires at each end of braided tube 400 are then removed, pen marks are placed at approximately 10 mm intervals along the entire length of the helically wrapped tube, and the tube/rod assembly can be placed into an air convection oven set at approximately 70° C. for a minimum of 15 minutes.

After the passing of a minimum of 15 minutes the tube/rod assembly is removed from the oven and, while still warm, the tube is axially compressed until the pen marks placed at the approximately 10 mm intervals are spaced consistently at approximately 6.5 mm intervals. The 15 minute, 70° C. parameters are chosen to facilitate the axial compression. Any suitable time and temperature combination may be utilized. During the compression, the braid pattern of the tube 400 densifies and small corrugations form along the surface of the tube. The PTFE film, however, serves to substantially maintain the reduced diameter of braided tube 400 during the axial compression inhibiting the formation of gross corrugations. With braided tube 400 axially compressed, the tube/rod assembly is preferably placed into an air convection oven set at approximately 197° C. for approximately 3.5 minutes and then removed to cool to ambient temperature. Once cool, the PTFE film is removed and braided tube 400 is carefully removed from the rod. At this point the braided tube is capable of undergoing an increase in diameter without a substantial change in length.

The 3.5 minute 197° C. treatment imparts a thermal set into braided tube 400, without substantially melting or bonding the strands of the tube, rendering the tube substantially dimensionally stable and easily handled. Any suitable time and temperature combination may be utilized. In some embodiments a more aggressive thermal treatment may be preferred or required such that all or portions of the material (s) used soften and mildly bond to one another. FIG. 4C shows an enlarged illustration of the compression of the braid pattern of braided tube 400.

As previously stated any suitable time/temperature combinations may be utilized in the various thermal treatment and axial compression steps described above. Additionally, any suitable means of achieving the compression of the braid pattern of braided tube 400 may be employed. For example, braided tube 400 may be placed within a glass tube having an inner diameter appropriate to cause braided tube 400 to assume an axially elongated/reduced diameter condition. A rod of appropriate material and diameter may then be fitted coaxially within braided tube 400. Preferably, the rod is slidable yet snugly fit within braided tube 400. The glass tube/rod assembly may then be suitably heated. With the glass tube/rod assembly heated, tubing of appropriate material, having an outer diameter able to be inserted within the glass tube and having an inner diameter able to accommodate the rod, may be inserted into each end of the glass tube. Preferably, the tubing is slidable within the glass tube and over the rod yet snugly fit to both, acting in a fashion similar to a piston within the glass tube. The tubing at each end of the glass tube may then be slid toward the center of the glass tube causing braided tube 400 to axially compress to the desired amount. Next, the axially compressed braided tube 400, while in the glass tube, may be suitably thermally treated, then allowed to cool and removed form the glass tube.

Regardless of the technique employed to achieve the axial compression, various embodiments of balloon 114 may include middle layers with any suitable amount of axial compression. For example, if a braided tube is used within the balloon embodiment the amount of axial compression desired may depend on the braid pattern of the tube. Some braid patterns may not be constant along the length of the braided tube and, as such, may require different amounts of axial compression along the length of the tube. Varying degrees of axial compression may result in varying degrees of corrugations. The formation of the corrugations may also be dependent on the technique employed to achieve the axial compression. In some embodiments of balloon 114 suitable axial compression may be achieved without any formation of corrugations.

In some embodiments, it may be desirable for balloon 114 to either shorten or lengthen as it is inflated. For example, if balloon catheter 100 is used to deploy a stent that shortens as it grows in diameter, it may be desirable for balloon 114 to shorten in unison with the stent during deployment. Conversely, in such an application of balloon catheter 100, it may be desirable for balloon 114 to slightly lengthen during inflation to counteract the shortening of the stent being deployed.

With the axially compressed braided tube 400 completed, one layer is fitted over the silicone tubing comprising inner layer 302. In this exemplary embodiment braided tube 400 is somewhat loose over inner layer 302, so the layer of braided tube 400 while over the silicone tubing comprising inner layer 302 is helically wrapped with PTFE film resulting in a more snug fit between the two. The PTFE wrapped inner layer 302 and layer of braided tube 400, while on the approximately 1.19 mm diameter rod, are placed within an air convection set at approximately 197° C. for approximately 3.5 minutes then removed and allowed to cool to ambient temperature. Once cool, the PTFE film is removed. Another layer of braided tube 400 is then placed over the first and the helical wrapping, the thermal treatment, the cooling, and the removal of the wrapping film are all repeated. Thus 2 layers of braided tube 400 are applied to the inner layer 302.

Next, outer layer 306 is applied by covering the outer surface of the 2 layers of compressed braided tube 400 with 2 coats of a 1:1 mixture of MED-1511 Adhesive Silicone (which may be sourced from NuSil of Carpinteria, Calif.) and Heptane. The 1:1 mixture is measured by weight. In this exemplary embodiment of balloon 114 outer layer 306 is intended to encapsulate middle layer 304 and bond to inner layer 302 thus unifying the individual layers into a composite tubular structure. During careful application of the first coat, the mixture penetrates through both layers of the treated braided tube 400 thus coming into contact with inner layer 302. Once the first coat of the mixture is applied it is allowed to cure in a high humidity environment for a minimum of 18 hours. A second coat of the same silicone/heptane mixture is then applied over the first coat and cured in the same manner as the first coat.

While in this embodiment outer layer 306 comprises a silicone mixture which after curing results in a uniform silicone layer, any suitable material or combination of materials may be used. Such materials include but are not limited to latex, polyurethane, PEBA, and/or fluoroelastomers. Additionally, various methods or combinations of methods may be employed to create a suitable outer layer 306. For example, outer layer 306 may comprise a suitable silicone tube that may be fitted coaxially over layers 302 and 304, and that may be attached to the layers by various elastomers applied as adhesives. Conversely, outer layer 306 may not be attached, or may only be partially attached to layers 302 and/or 304. Other methods for the creation of an outer layer 306 include, but are not limited to, dipping, application by spraying, and/or molding. Some embodiments of balloon 114 may utilize extrusion as method of creating outer layer 306 over layers 302 and 304. It may be advantageous in some embodiments to extrude or otherwise mold a suitable material around a treated braided tube or other suitable middle layer 304, thus creating layers 302 and 306 with one process. Furthermore, some embodiments of balloon 114 may provide outer layer 306 with regions of porosity that allow the passage of fluids there through while still allowing balloon 114 to be inflated.

Once the second coat is cured, the exemplary balloon 114 is completed. This particular embodiment of balloon 114 is produced to create a liquid tight balloon material. Further processing, however, may be completed in order to create regions of porosity within the balloon material. The processing may completed in any suitable manner, for example, the balloon material may be treated by a laser to create holes of a controlled diameter, or holes may be created with pins. As previously mentioned, the regions of porosity may allow various therapeutic agents to be delivered to bodily conduits while allowing the balloon to inflate.

When the second coat is cured the exemplary balloon 114 is carefully removed from the approximately 1.19 mm diameter rod. To facilitate the removal of balloon 114 from the rod, small portions of each end of the balloon 114 may be cut off and the rod may be placed in a bath of isopropyl alcohol. The isopropyl alcohol penetrates between the balloon 114 and the rod thus providing lubrication during the removal process. After removal from the rod, the alcohol is allowed to evaporate from the exemplary embodiment of balloon 114.

A segment of the exemplary balloon 114, approximately 30 mm long, is then cut. In order to measure the inflation characteristics (compliance) of the balloon, blunt needles having an outer diameter of approximately 1.3 mm and equipped with luer fittings are inserted into each end of the segment of exemplary balloon 114. Tuohy-Borst adapters (part mx220, manufactured by Medex, Hilliard, Ohio) may be used to create a watertight seal between the needles and the exemplary balloon 114. One needle is sealed with a luer cap, while the other is connected to a hand-held inflation syringe filled with water.

Prior to any inflation, the distance between the two Tuohy-Borst adapters is measured to be approximately 18.27 mm. Also, the outer diameter of the balloon is measured to be approximately 2.36 mm. The balloon is then inflated, at ambient temperature, in increments of approximately 0.1 MPa (1 atm) and the outer diameter of the balloon is measured at each increment until a pressure of approximately 0.6 MPa (6atm) is achieved. During the inflation, the distance between the Tuohy-Borst adapters is measured to be 18.43 and 18.98 mm at approximately 0.4 and 0.6 MPa (4 and 6 atm) respectively. These data translate into a maximum change in length during inflation of 0.71 mm which, when expressed as a percentage of the balloon length prior to inflation, is approximately 4%. Once all of the measurements are taken, the exemplary balloon 114 is deflated and the outer diameter and distance between the Tuohy-Borst adapters are measured to be 2.31 and 18.27 mm respectively, indicating that the exemplary balloon exhibits an elastic response returning to nearly its original dimensions after being inflated.

The same test procedure is repeated, yielding compliance data for the exemplary balloon 114 during a second inflation. During this second inflation the distance between the Tuohy-Borst adapters is measured to be 18.58 mm at approximately 0.4 MPa (4 atm), showing a small change in length similar to that of the first inflation. All diameter and length measurements are taken with a pair of digital calipers.

With the second inflation completed, the blunt needles and Tuohy-Borst adapters are removed and barbed luer fittings (for example, part FTLL210-9 manufactured by Value Plastics Inc., Fort Collins, Colo.) are inserted into each end of the length of exemplary balloon 114. Wax-coated thread is then tied around each end, providing a watertight seal between the barbed luer fittings and the balloon. Next, one barbed luer fitting is sealed with a luer cap while the other is connected to a hand-held inflation syringe filled with water and the balloon is inflated until rupture occurs.

The exemplary embodiment of balloon 114 ruptures at approximately 0.8 MPa (8 atm). When tested in the same manner, the silicone tubing comprising inner layer 302 ruptures at approximately 0.1 MPa (1 atm). Therefore, the addition of the 2 layers of treated braided tube 400 (inner layer 304) and outer layer 306 results in an approximately eight-fold increase in burst strength.

FIG. 5 shows the compliance characteristics of the exemplary embodiment of balloon 114. As shown in FIG. 5, the compliance signature of exemplary balloon 114 during the first inflation is clearly different from that of the balloon during the second inflation. During the first inflation, most of the diameter growth of exemplary balloon 114 occurs between approximately 0.3 and 0.6 MPa (3 and 6 atm), while very little diameter growth occurs between approximately 0 and 0.3 MPa (0 and 3 atm). During the second inflation, most of the diameter growth of the exemplary balloon occurs between approximately 0 and 0.2 MPa (0 and 2 atm), with a significant change in the slope of the compliance curve occurring at approximately 0.2 MPa (2 atm). The difference in the two compliance signatures is an aspect of balloon 114 that may be tailored and employed to enhance usage of balloon catheter 100.

For example, referring to FIGS. 1 and 6A, the distal portion of balloon catheter 100 may be placed within inflation mold 602 with balloon 114 centered lengthwise with respect to the large diameter cavity within the mold. The embodiment of mold 602 may be sized such that the large cavity is approximately half of the length of balloon 114 and of approximately the nominal inflated diameter of the balloon. Balloon 114 may then be inflated within the mold causing the balloon material to adopt the shape of the mold. In this manner, the center region of the balloon 114, having been inflated to its nominal diameter, will have a compliance signature corresponding to the second inflation curve as shown in FIG. 5. The end regions of the balloon, not having been inflated to a substantially larger diameter, will have a compliance signature corresponding to the curve of the first inflation. Balloon 114 after such a treatment essentially exhibits regions of varying compliance.

Balloon 114, treated by inflation within mold 602, may provide enhanced control during an angioplasty procedure. For example, if the balloon catheter 100 is being used to remodel a stenotic lesion of relatively short length, balloon 114 may be placed, centered lengthwise with respect to the lesion. Upon inflation, the center of balloon 114 inflates first, coming into contact with the stenotic tissue and initiating the angioplasty process. The end regions of balloon 114, changing in diameter at a lesser rate, remain smaller than the center and do not contribute to the remodeling of the stenotic tissue. Eventually, with increasing pressure all of the regions of balloon 114 reach approximately the same diameter.

FIG. 6B shows an inflation mold 608 wherein one half of the mold is of a larger inner diameter than the other half. The larger diameter half of inflation mold 608 may be of approximately the nominal inflated diameter of the balloon 114. Such an embodiment of an inflation mold, employed in a fashion similar to that described above, may be utilized to create an embodiment of balloon 114 that inflates at a faster rate at one end. Such an embodiment of balloon 114 may enhance the angioplasty process by not only pressurizing and expanding diseased blood vessels, but by also redistributing the diseased tissue in a predetermined lengthwise manner. Such an embodiment of balloon 114 may be utilized, for example, in situations wherein an occlusive lesion is located very close to the origin of a side-branch vessel and redistribution of the diseased tissue away from the side-branch vessel origin is highly advantageous.

While inflation molds 602 and 608 each have a region that allows an embodiment of balloon 114 to inflate to approximately its fully inflated diameter, embodiments of inflation molds may be created that allow the balloon to inflate only partially. For example, a balloon with a fully inflated diameter of approximately 6 mm may only be allowed to inflate to approximately 4 mm within a mold. Thus, various embodiments of inflation molds may be created. Any suitable inflation mold may be used to create any balloon embodiment having regions of distinct compliance characteristics. Conversely, it may be desirable in some instances to create balloon embodiments that have a single compliance characteristic throughout their entire length. This may be accomplished through the use of an embodiment of an inflation mold having a constant inner diameter. It is to be understood that an inflation mold is not required when an inflation process is used to affect the compliance characteristics of the balloon.

While any suitable inflation mold geometry may be employed to create any desired balloon embodiment, certain inflation mold embodiments may be used more commonly than others. In order to facilitate routine usage of inflation molds to customize the compliance characteristics of various embodiments of balloon 114, it may be desirable or otherwise advantageous to provide a set or a kit of inflation molds having commonly used geometries to physicians. In this manner, a single embodiment of a balloon provided by a manufacturer may, by virtue of being customized, be transformed into various embodiments each particularly treated to meet a specific need. In some embodiments it may be desirable to combine the aspect of treating a balloon by inflating it within a mold, with varying the materials or the amount of materials utilized along the balloon length. Such combinations may be utilized to create embodiments of balloon 114 with dramatically different regions of compliance. For example, an embodiment of balloon 114 wherein middle layer 304 is twice as thick at one half of the balloon length may be created. Each half of such an embodiment of balloon 114 would have distinct compliance characteristics than the other, the half with the thinner middle layer 304 being the more compliant of the two. The embodiment of balloon 114 may then be situated within inflation mold 608 such that the half of the balloon with the thicker region of middle layer 304 is located within the region of smaller diameter within mold 608 and suitably inflated within the mold. In such a manner, two of the described aspects may be combined to create various balloon embodiments with regions of different compliance. Balloon embodiments with regions of different compliance that include regions of porosity for the delivery of therapeutic agents may also be created.

Additionally, the aspect of treating a balloon by inflating it within a mold may be combined with utilizing a braid or other textile having any suitable geometry such as, but not limited to, tapers or teardrop shapes to create balloon embodiments that are suited to specific bodily conduit geometries. Such balloon embodiments may also include regions of porosity for the delivery of therapeutic agents.

Any suitable method of attachment may be employed to connect the various embodiments of balloon 114 to the various embodiments of the catheter member(s) in order to create various embodiments of balloon catheter 100. For example, in the exemplary embodiment of balloon 100 described above, balloon 114 may be attached to steps 202 and 204 (FIG. 2) with various adhesives or combinations of adhesives such as, but not limited to, cyanoacrylates, or adhesives that are cured via ultra-violet light. In some embodiments of balloon catheter 100, balloon 114 may be thermally bonded to the catheter member(s).

Various techniques may be employed to enhance the connection between balloon 114 and the catheter member(s). For example, reinforcing bands made in any suitable configuration of any suitable material may be placed around balloon 114 coincident to the points at which the balloon is attached to the catheter member(s). Alternatively, the regions of attachment may be wrapped by reinforcing filaments of any suitable material. Usage of thin films may also yield advantageous embodiments.

Some embodiments of balloon catheter 100 may take advantage of multi-layer embodiments of balloon 114 by integrating any number of any of the balloon layers into the catheter member(s). For example, in the exemplary embodiment of balloon 114 shown in FIG. 3, middle layer 304 may extend beyond the edges of layers 302 and 306. The portions of middle layer 304 extending beyond the other balloon layers may be integrated into inner and outer catheter members 108 and 110 respectively or into any other suitable catheter member(s).

By way of further example, a desired length of an embodiment of inner layer 302 may be attached by any suitable method to steps 202 and 204, or to any suitable embodiment of the catheter member(s). An embodiment of middle layer 304, suitably longer than inner layer 302 may then be fitted coaxially over inner layer 302. Additional catheter member material may then be applied over the regions of middle layer 304 that extend beyond the edges of inner layer 302. The additional catheter material may be applied by any suitable method. For example, the additional material may be injection molded over the regions of middle layer 304 that extend beyond the edges of inner layer 302. Alternatively, thin tubing may be applied over the regions of middle layer 304 that extend beyond the edges of inner layer 302. The thin tubing may be attached to the middle layer 304 as well as the catheter member(s) by any suitable method such as the use of an adhesive or various thermal bonding techniques. Various embodiments of distal tip 116 may be formed in such a manner. With middle layer 304 suitably integrated into the catheter member(s), outer layer 306 may be applied by any suitable method such as, but not limited to, application in the form of a mixture (as described above), or alternatively outer layer 306 may comprise a tube similar to inner layer 302. Regardless of embodiment, outer layer 306 may extend onto the catheter member(s) if desired. Integration of one or more layers of balloon 114 into the catheter member(s) may be advantageous by providing a very sleek profile to the distal region of balloon catheter 100 as well as a very reliable and strong connection between balloon 114 and the catheter member(s).

The present invention has been described above with reference to various exemplary embodiments. However, changes and modifications may be made to various exemplary embodiments without departing from the scope of the present invention. For example various embodiments of the distal portion of balloon catheter 100, particularly with regard to the arrangement of catheter members 108 and 110 and balloon 114 may be provided. Additionally, various changes in the configuration and the materials of balloon 114 may be provided. These and other changes or modifications are intended to be included within the scope of the present invention as set forth in the appended claims.

What is claimed is:

1. A balloon for use in a catheter, comprising:
a tube having a first layer of a textile material, the textile material being treated such that the tube is adapted to experience a change in diameter while remaining substantially the same length when inflated.

2. The balloon as recited in claim 1, wherein the first layer comprises a continuous tube.

3. The balloon as recited in claim 1, wherein the first layer comprises a braided textile material.

4. The balloon as recited in claim 3, wherein the braided textile material comprises strands running parallel to a major axis of the tube.

5. The balloon as recited in claim 3, wherein the braided textile material comprises metallic elements.

6. The balloon as recited in claim 3, wherein the braided textile material is comprised of a material selected from a group consisting of polyester, nylon, polyethylene, carbon, kevlar, PEBA and PTFE.

7. The balloon as recited in claim 1, further comprising a second layer disposed in cooperative relation to the first layer.

8. The balloon as recited in claim 7, wherein the second layer comprises a porous material.

9. The balloon as recited in claim 7, wherein the second layer comprises a liquid tight material.

10. The balloon as recited in claim 7, wherein the second layer is comprised of a material selected from a group consisting of silicone, latex, polyurethane, PEBA, and fluorelastomers.

11. The balloon as recited in claim 7, wherein the first layer comprises a continuous tube.

12. The balloon as recited in claim 7, wherein the first layer partially overlays the second layer.

13. The balloon as recited in claim 12, wherein the first layer comprises helically arranged strips of material.

14. The balloon as recited in claim 12, wherein the first layer comprises strips of material arranged in a lengthwise direction.

15. The balloon as recited in claim 7, further comprising a third layer wherein the first layer is disposed generally intermediate the third layer and the second layer.

16. The balloon as recited in claim 15, wherein the third layer is bonded to the second layer.

17. The balloon as recited in claim 15, wherein the third layer and the second layer each comprise a porous material.

18. The balloon as recited in claim 15, wherein the third layer and the second layer each comprise a liquid tight material.

19. The balloon as recited in claim 15, wherein the third layer and the second layer each comprise a material selected from a group consisting of silicone, latex, polyurethane, PEBA, and fluorelastomers.

20. The balloon as recited in claim 15, wherein the first layer comprises a continuous tube.

21. The balloon as recited in claim 15, wherein the first layer partially overlays the second layer.

22. The balloon as recited in claim 21, wherein the first layer comprises helically arranged strips of material.

23. The balloon as recited in claim 7, wherein the layers cooperate to provide the tube with varying compliance characteristics over its length.

24. The balloon as recited in claim 23, wherein the layers have varying thickness to vary the compliance characteristics.

25. The balloon as recited in claim 23, wherein the layers are comprised of various materials to vary the compliance characteristics.

26. The balloon as recited in claim 7, wherein the layers cooperate such that the tube has compliance characteristics that are generally uniform over its length.

27. The balloon as recited in claim 23, wherein the compliance characteristics of the layers are varied using an inflation process.

28. A method of making a balloon for use in a catheter, comprising:
forming a tube having a first layer of a textile material; and
treating the textile material to cause the tube to experience a change in diameter while remaining substantially the same length when inflated.

29. The method as recited in claim 28, further comprising placing the first layer generally intermediate a second layer and a third layer.

30. The method as recited in claim 28, further comprising bonding the second layer to the third layer.

31. The method as recited in claim 28, further comprising using an inflation process to vary the compliance characteristics of the balloon.

32. The method as recited in claim 28, further comprising using different materials when constructing the first layer to vary the compliance characteristics of the balloon.

33. The method as recited in claim 28, further comprising using materials of different densities when constructing the first layer to vary the compliance characteristics of the balloon.

34. The method as recited in claim 28, further comprising using varying amounts of material when constructing the first layer to vary the compliance characteristics of the balloon.

35. The method as recited in claim 28, wherein the compliance characteristics are uniform over the length of the balloon.

36. A balloon catheter, comprising:
a catheter having a first portion and a second portion;
a balloon disposed between the first portion and the second portion, the balloon having a first layer of a textile material, the textile material being treated such that the balloon is adapted to experience a change in diameter while remaining substantially the same length when inflated.

37. The catheter as recited in claim 36, wherein the ends of the balloon are restrained by the first portion and the second portion thus rendering the ends essentially nondistensible.

38. The catheter as recited in claim 36, wherein the first layer comprises a braided textile material.

39. The catheter as recited in claim 36, wherein the first layer comprises a a continuous tube.

40. The catheter as recited in claim 36, wherein the first layer comprises strands running parallel to a major axis of the balloon.

41. The catheter as recited in claim 36, wherein the first layer comprises metallic elements.

42. The catheter as recited in claim 36, wherein the first layer is comprised of a material selected from a group consisting of polyester, nylon, polyethylene, carbon, kevlar, PEBA and PTFE.

43. The catheter as recited in claim 36, further comprising a second layer disposed in cooperative relation to the first layer.

44. The catheter as recited in claim 43, wherein the second layer comprises a porous material.

45. The catheter as recited in claim 43, wherein the second layer comprises a liquid tight material.

46. The catheter as recited in claim 43, wherein the second layer is comprised of a material selected from a group consisting of silicone, latex, polyurethane, PEBA, and fluorelastomers.

47. The catheter as recited in claim 43, wherein the first layer comprises a continuous tube.

48. The catheter as recited in claim 43, wherein the first layer partially overlays the second layer.

49. The catheter as recited in claim 48, wherein the first layer comprises helically wound strips of material.

50. The catheter as recited in claim 43, further comprising a third layer wherein the first layer is disposed generally intermediate the third layer and the second layer.

51. The catheter as recited in claim 50, wherein the third layer is bonded to the second layer.

52. The catheter as recited in claim 50, wherein the third layer and the second layer each comprise a porous material.

53. The catheter as recited in claim 50, wherein the third layer and the second layer each comprise a liquid tight material.

54. The catheter as recited in claim 50, wherein the third layer and the second layer each comprise a material selected from a group consisting of silicone, latex, polyurethane, PEBA, and fluorelastomers.

55. The catheter as recited in claim 50, wherein the first layer comprises a continuous tube.

56. The catheter as recited in claim 50, wherein the first layer partially overlays the second layer.

57. The catheter as recited in claim 56, wherein the first layer comprises helically wound strips of material.

58. The catheter as recited in claim 50, wherein the balloon has varying compliance characteristics over its length.

59. The catheter as recited in claim 58, wherein the balloon has varying thickness to vary the compliance characteristics.

60. The catheter as recited in claim 50, wherein the balloon is comprised of various materials to vary the compliance characteristics.

61. The catheter as recited in claim 36, wherein an adhesive is used to attach the balloon to at least one of the first portion and the second portion.

62. The catheter as recited in claim 36, wherein the balloon is thermally bonded to at least one of the first portion and second portion.

63. The catheter as recited in claim 36, further comprising reinforcing bands placed around the balloon coincident with at least one of the first portion and the second portion.

64. The catheter as recited in claim 36, further comprising reinforcing filaments placed around the balloon coincident to at least one of the first portion and second portion.

65. The catheter as recited in claim 36, further comprising reinforcing strips of thin film placed around the balloon coincident to at least one of first portion and the second portion.

66. The catheter as recited in claim 36, wherein the balloon is integrally attached to at least one of the first portion and the second portion.

67. The balloon as recited in claim 27, wherein the compliance characteristics of the layers are varied using a mold during the inflation process.

68. The method as recited in claim 28, further comprising inflating the balloon in a mold to vary the compliance characteristics of the balloon.

69. The balloon as recited in claim 1, wherein the first layer comprises a predetermined shape.

70. The balloon as recited in claim 69, wherein the predetermined shape comprises a tapered portion.

71. The balloon as recited in claim 69, wherein the predetermined shape comprises a tear-drop shaped portion.

72. The method as recited in claim 31, further comprising using a mold during the inflation process to vary the compliance characteristics of the layers.

73. A balloon for use in a catheter, comprising:

a tube having a first layer of a textile material, the textile material being treated such that the tube is adapted to experience a change in diameter while experiencing a controlled change in length when inflated.

74. A balloon for use in a catheter, comprising:

a tube having a first layer of a braided material, the braided material being treated such that the tube is adapted to experience a change in diameter while remaining substantially the same length when inflated.

75. The balloon as recited in claim 74, wherein the braided material comprises strands running parallel to a major axis of the tube.

76. The balloon as recited in claim 74, wherein the braided material comprises metallic elements.

77. The balloon as recited in claim 74, wherein the braided material is comprised of a material selected from a group consisting of polyester, nylon, polyethylene, carbon, kevlar, PEBA and PTFE.

78. A balloon for use in a catheter, comprising:

a tube having a first layer of a textile material, the textile material being treated such that tube experiences a change in diameter primarily via an increase in a surface area of the tube while remaining substantially the same length when inflated.

79. A balloon for use in a catheter, comprising:

a tube having a first layer of a braided material, the braided material being treated such that the tube experiences a change in diameter primarily via an increase in a surface area of the tube while remaining substantially the same length when inflated.

80. The balloon as recited in claim 1, wherein the balloon is adapted to remain substantially the same length when inflated at a time prior to its use in connection with the catheter.

81. The balloon catheter as recited in claim 36, wherein the balloon is adapted to remain substantially the same length when inflated at a time prior to its use in connection with the catheter.

82. The balloon as recited in claim 73, wherein the balloon is adapted to experience a controlled change in length when inflated at a time prior to its use in connection with the catheter.

83. The balloon as recited in claim 72, wherein the balloon is adapted to remain substantially the same length when inflated at a time prior to its use in connection with the catheter.

* * * * *